(12) United States Patent
Chung

(10) Patent No.: US 10,478,392 B2
(45) Date of Patent: Nov. 19, 2019

(54) PEPTIDE AND COSMETIC COMPOSITION COMPRISING SAME FOR PREVENTING SKIN AGING OR SKIN WRINKLE FORMATION

(71) Applicant: College of Medicine Pochon CHA University Industry-Academic Cooperation Foundation, Pocheon-si, Gyeonggi-do (KR)

(72) Inventor: Ji-Hyung Chung, Seoul (KR)

(73) Assignee: College of Medicine Pochon CHA University Industry-Academic Cooperation Foundation, Pocheon-si, Gyeonggi-do (KR)

( * ) Notice: Subject to any disclaimer, the term of this patent is extended or adjusted under 35 U.S.C. 154(b) by 0 days.

(21) Appl. No.: 15/771,222

(22) PCT Filed: Oct. 27, 2016

(86) PCT No.: PCT/KR2016/012167
§ 371 (c)(1),
(2) Date: Apr. 26, 2018

(87) PCT Pub. No.: WO2017/074059
PCT Pub. Date: May 4, 2017

(65) Prior Publication Data
US 2018/0325794 A1 Nov. 15, 2018

(30) Foreign Application Priority Data
Oct. 27, 2015 (KR) .................. 10-2015-0149115

(51) Int. Cl.
*A61K 8/64* (2006.01)
*C07K 7/08* (2006.01)
*A61Q 19/08* (2006.01)

(52) U.S. Cl.
CPC ............... *A61K 8/64* (2013.01); *A61Q 19/08* (2013.01); *C07K 7/08* (2013.01)

(58) Field of Classification Search
CPC .................................. A61K 8/64; C07K 7/08
See application file for complete search history.

(56) References Cited

U.S. PATENT DOCUMENTS

2016/0222077 A1 8/2016 Hahn et al.

FOREIGN PATENT DOCUMENTS

| KR | 10-2013-0099480 A | 9/2013 |
| KR | 10-2014-0090756 A | 7/2014 |
| KR | 10-2015-0011726 A | 2/2015 |
| KR | 10-2015-0029884 A | 3/2015 |

OTHER PUBLICATIONS

Waite, 1983, Evidence for a Repeating 3,4,-Dihydroxyphenylalanine- and Hydroxyproline-containing Decapeptide in the Adhesive Protein of the Mussel, *Mytilus edulis* L., The Journal of Biological Chemistry, 258(5): 2911-2915.*

Filpula et al., 1990, Structural and Functional Repetition in a Marine Mussel Adhesive Protein, Biotechnol Prog, 6: 171-177.*

* cited by examiner

*Primary Examiner* — Amber D Steele
(74) *Attorney, Agent, or Firm* — Vorys, Sater, Seymour & Pease LLP; Min Suhn Koh

(57) ABSTRACT

Provided herein is a peptide, a cosmetic composition comprising the same, and a method for inhibiting skin-aging or skin-wrinkle formation using the same, the peptide having activities for facilitating the bindings between keratinocytes; and increasing the expressions of junction proteins.

5 Claims, 4 Drawing Sheets
Specification includes a Sequence Listing.

PEPTIDE AND COSMETIC COMPOSITION COMPRISING SAME FOR PREVENTING SKIN AGING OR SKIN WRINKLE FORMATION

SEQUENCE LISTING

The Sequence Listing submitted in text format (.txt) filed on Apr. 26, 2018, named "SequenceListing.txt", created on Apr. 20, 2018 (1.27 KB), is incorporated herein by reference.

TECHNICAL FIELD

The present invention relates to a novel peptide and a cosmetic composition for inhibiting a skin-aging or a skin-wrinkle formation comprising the same. The peptide has activities for facilitating the bindings between keratinocytes; and increasing the expressions of junction proteins.

BACKGROUND ART

Human skin consists of epidermis and dermis, besides the outermost layer thereof (keratin); and hypodermis containing adipose tissues resides thereunder. The epidermis consists mainly of keratinocytes; and the dermis consists mainly of dermal fibroblasts.

Functional cosmetic materials targeting for ameliorating wrinkle and inhibiting skin aging are mainly natural products, chemical compounds and peptides for facilitating the expression of collagen proteins in the dermal fibroblasts (major cells of the dermis) or inhibiting the proteases against collagen proteins; in addition to proteins such as growth factors, cytokines and the like, for facilitating the growth of dermal cells. However, it is well known in the art that it is very difficult for most active materials having such effects to pass through the epidermis of the skin and reach the dermis.

The epidermis acts as a barrier for preventing the permeation of external harmful substances, ultraviolet, chemical substances, and so on and maintaining the moisturization in the skin. The major cell functioning as such is keratinocytes and it is known in the art that keratinocytes regulate immune responses in the sub-dermal tissues by secreting inflammatory regulators (cytokines, chemokines, etc.), along with maintaining the skin barrier. It is known in the art that such a skin barrier function of the epidermis is originated from the bindings between keratinocytes, i.e., the expression and activation of cell-to-cell junction proteins. The junction proteins function as an important barrier not only for providing a primary physical defense from external infections, but also for protecting dermal cells and inhibiting immune imbalance from chemical stimulations inside or outside the cells. The junction proteins are usually divided into four groups: tight junction proteins, adherence junction proteins, gap junction proteins, and desmosomes. Among them, tight junction proteins (e.g., claudins, occludins, ZO-1, 2, etc.) are known as a major factor contributing to the cell barrier protection, by preventing the migration of molecules, especially water-soluble materials, through the space between cells; and inhibiting cell permeability. Therefore, it is expected that a material capable of facilitating the bindings between keratinocytes and/or increasing the expressions of junction proteins may be useful for inhibiting a skin-aging or a skin-wrinkle formation, through protection and activation of the skin barrier.

DISCLOSURE

Technical Problem

The present inventors have synthesized various peptide fragments and evaluated the activities thereof. As the results thereof, it has been found that the peptide fragments having specific sequences show activities for facilitating the bindings between keratinocytes effectively; and increasing the expressions of junction proteins significantly.

Therefore, it is an object of the present invention to provide said peptide fragments.

It is another object of the present invention to provide a cosmetic composition for inhibiting a skin-aging or a skin-wrinkle formation, comprising said peptide fragments.

Technical Solution

In accordance with an aspect of the present invention, there is provided a peptide having any one of amino acid sequences of SEQ ID NOs: 1 to 3.

In accordance with another aspect of the present invention, there is provided a cosmetic composition for inhibiting a skin-aging or a skin-wrinkle formation, comprising a peptide having any one of amino acid sequences of SEQ ID NOs: 1 to 3.

Advantageous Effects

It has been found by the present invention that the specific peptide fragments, i.e., the peptides as set forth in SEQ ID NOs: 1 to 3, show activities for facilitating the bindings between keratinocytes effectively; and increasing the expressions of junction proteins significantly. Therefore, the peptides can be usefully applied to a cosmetic composition for inhibiting a skin-aging or a skin-wrinkle formation.

BRIEF DESCRIPTION OF THE DRAWINGS

FIG. 1 show the results obtained by evaluating the binding efficacies between keratinocytes through the cell-cell interaction assays using human epidermal keratinocytes.

In FIG. 2, Lane 1 shows the result of the peptide non-treated group (Control group); and Lanes 2, 3, and 4 show the results of the test groups treated with the peptide of SEQ ID NO: 1 (Lane 2), 2 (Lane 3), or 3 (Lane 4) in 100 nM, respectively.

BEST MODE

Figure 1A:
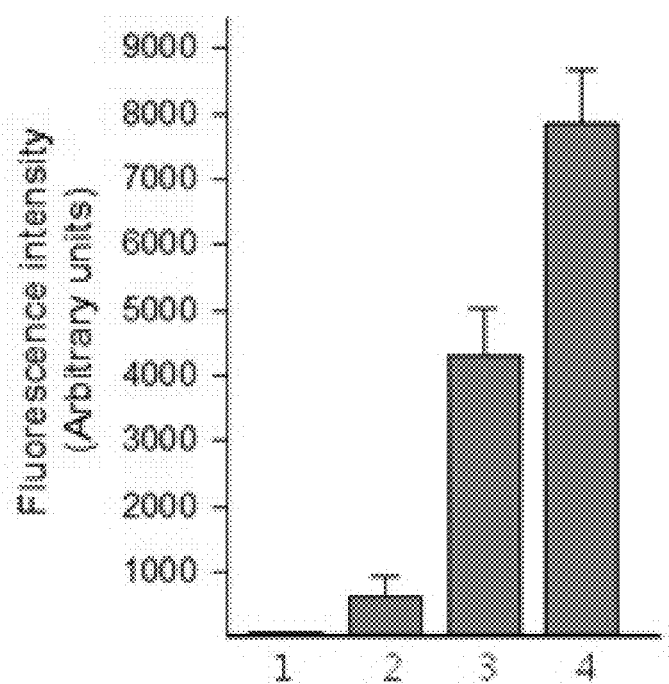
FIGS. 1a to 1c are the results obtained by treating the peptides of SEQ ID NOs: 1, 2 and 3, respectively, in the test groups. In the respective FIGS. 1a to 1c, Lane 1 shows the result of the group in which the cultured cells were not treated with the binding cells (i.e., the stained cells) (Control group 1); Lane 2 shows the result of the group in which the cultured cells were treated with the binding cells (i.e., the stained cells) (Control group 2); Lane 3 shows the result of the group in which the cultured cells pre-treated with the peptide of SEQ ID NO: 4 (control peptide) were treated with the binding cells (i.e., the stained cells) (Control group 3); and Lane 4 shows the result of the group in which the cultured cells pre-treated with the peptide of SEQ ID NO: 1, 2 or 3 were treated with the binding cells (i.e., the stained cells) (Test group).

As used herein, the term, "skin aging" refers to the skin aging(s) caused by intrinsic and external factors, including for example the skin photoaging(s) accompanied by skin-wrinkle formation, preferably the skin photoaging(s) due to ultraviolet stimulation accompanied by skin-wrinkle formation.

And also, the "skin wrinkle" refers to the wrinkles formed on the skin (wrinkle formation on skin).

The present invention provides a peptide having any one of amino acid sequences of SEQ ID NOs: 1 to 3.

And also, the present invention provides a cosmetic composition for inhibiting a skin-aging or a skin-wrinkle formation, comprising a peptide having any one of amino acid sequences of SEQ ID NOs: 1 to 3.

The present inventors have synthesized various peptide fragments and evaluated the activities thereof. Surprisingly, it has been found that the peptide fragments having specific sequences, i.e., the peptide as set forth in SEQ ID NOs: 1 to 3, not only facilitate physical bindings between the keratinocytes, major cells in the epidermis, which contribute to protection and activation of the skin barrier, but also increase the expressions of junction proteins significantly. Therefore, the peptides according to the present invention can be usefully applied to a cosmetic composition for improving a skin-aging and/or inhibiting a skin-wrinkle formation. The peptides as set forth in SEQ ID NOs: 1 to 3 may be synthesized according to conventional methods for synthesizing a peptide.

The cosmetic composition of the present invention may be in the form of a functional cosmetic composition comprising said peptides as an active ingredient. The cosmetic composition may be prepared in various forms according to conventional methods thereof. For example, the cosmetic composition may be prepared in forms of cosmetic products, cosmetic solutions, creams, lotions, etc. comprising said peptides, which may be diluted with a cleansing water, an astringent solution, or a moisture solution, for the use thereof. And also, the cosmetic composition may include conventional excipients, such as a stabilizer, a solubilizing agent, vitamins, a pigment, a flavoring agent, which are conventionally used in the field of cosmetic composition. In the cosmetic composition, the peptides may be present in an amount enough to provide improvement of a skin-aging and/or inhibition of a skin-wrinkle formation, for example in an amount ranging from 0.001 to 2 weight %, preferably about 0.1 to 2 weight %, based on the total weight of the composition.

Hereinafter, the present invention will be described more specifically by the following examples. However, the following examples are provided only for illustrations and thus the present invention is not limited to or by them.

Example 1: Synthesis of Peptides

The peptides of SEQ ID NOs: 1 to 4 in the following table 1 were synthesized with an automatic peptide synthesizer (PeptrEx-R48, Peptron, Daejeon, Korea) using a FMOC solid-phase method. The synthesized peptides were purified and analyzed by reverse-phase high-performance liquid chromatography (reverse-phase HPLC) (Prominence LC-20AB, Shimadzu, Japan) using a C18 analytical RP column (Shiseido capcell pak), and identified using a mass spectrometer (HP 1100 Series LC/MSD, Hewlett-Packard, Roseville, U.S.A.).

TABLE 1

| Peptide name* | SEQ ID NO | Amino acid sequence (sequence length) |
|---|---|---|
| AdhPep-5 | SEQ ID NO: 1 | GRGDSPGRALARG (13-mer) |
| AdhPep-10-2 | SEQ ID NO: 2 | AKPTYKAKPTYKAKPTYK (18-mer) |
| AdhPep-11-1 | SEQ ID NO: 3 | AYDPGYKAYDPGYK (14-mer) |

TABLE 1-continued

| Peptide name* | SEQ ID NO | Amino acid sequence (sequence length) |
|---|---|---|
| Control peptide | SEQ ID NO: 4 | GRGDSP (6-mer) |

*Peptide name: arbitral name for experiments

Example 2: Evaluation of the Binding Efficacies Between Keratinocyte

Figure 1B:
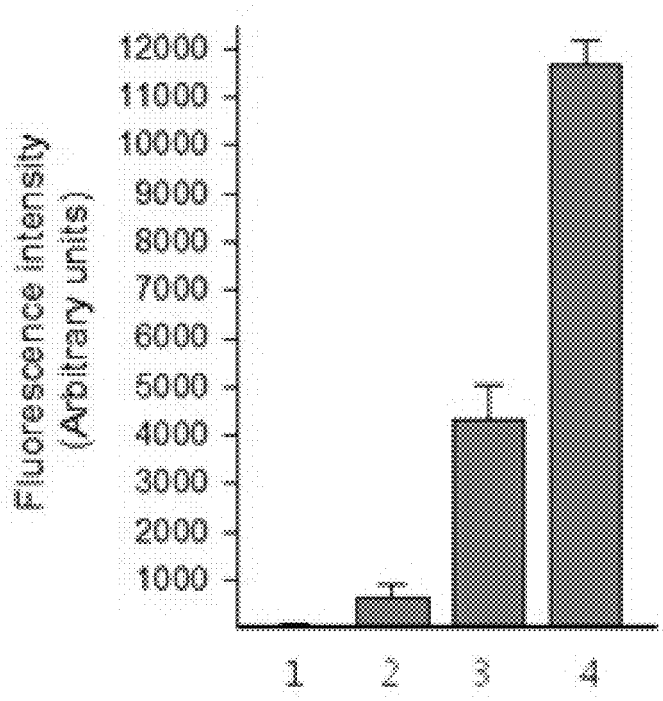
Figure 1C:
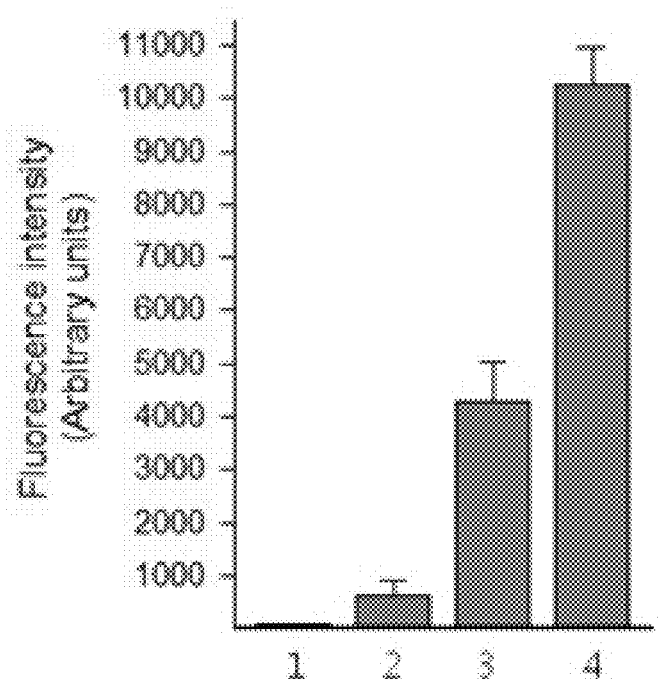

The cell-cell interaction assay was carried out in order to evaluate the binding efficacies between keratinocytes. Human epidermal keratinocytes (Thermo Fisher Scientific) were inoculated in the concentration of $5 \times 10^4$ cells in each well of a 24-well plate; and the EpiLife medium (Thermo Fisher Scientific) containing Human Keratinocyte Growth Supplement (Thermo Fisher Scientific) was added thereto. The cells were cultured in a $CO_2$ incubator for 24 hours. Each well was treated with the peptides of SEQ ID NOs: 1 and 4 in the concentration of 100 nM. After incubating for 40 minutes, the medium of each well was changed. Human epidermal keratinocytes were stained with Vybrant DiO Cell-labeling dye (Life Technologies). The stained cells ($1.5 \times 10^5$ cells) were treated to the peptide non-treated cells (Control group 2), to the cells treated with the peptide of SEQ ID NO: 4 (Control group 3), and to the cells treated with the peptide of SEQ ID NO: 1 (Test group), respectively, followed by incubating for 10 minutes. Control group 1 is the group to which the stained cells were not treated. After washing the cells of each group with phosphate-buffered saline (PBS) three times, the cells were detached with a cell stripper solution and then transferred to a black well plate. Each fluorescence intensity was measured at the wavelengths of 480/501 nm and the results thereof are shown in FIG. 1a. And also, the cell-cell interaction analyses were carried out in the same manner as in the above, using the peptides of SEQ ID NOs: 2 and 3, respectively, instead of the peptide of SEQ ID NO: 1; and the results thereof are shown in FIGS. 1b and 1c, respectively. As can be seen from the results shown in FIGS. 1a to 1c, the bindings between keratinocytes in the test groups treated with the peptides of SEQ ID NOs: 1 to 3 were remarkably increased, in comparison with that of the peptide non-treated group (Control group 1) or the group treated with the control peptide AdhPep-1 (GRGDSP) SEQ ID NO: 4 (Control group 3).

Figure 2:
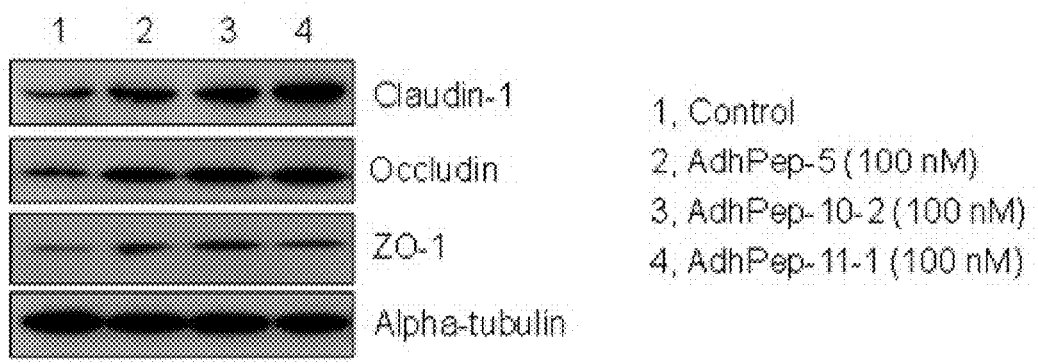
FIG. 2 shows the results obtained by immunoblot analyses of the junction protein expressions, according to treating human epidermal keratinocytes with the peptides of the present invention.

Example 3: Protein Expression According to Treating Keratinocytes with the Peptides Human epidermal keratinocytes (Thermo Fisher Scientific) were inoculated in the concentration of $5 \times 10^5$ cells in a 60 mm culture plate; and the EpiLife medium (Thermo Fisher Scientific) containing Human Keratinocyte Growth Supplement (Thermo Fisher Scientific) was added thereto. The cells were cultured for 24 hours. The cells were treated with the peptides of SEQ ID NOs: 1 to 3 in the concentration of 100 nM, respectively. After incubating for 24 hours, the medium was removed. After washing the cells with PBS, the cells were subject to cell lysis with a RIPA buffer (Sigma-Aldrich) containing protease inhibitor cocktail (Sigma-Aldrich), followed by centrifugation. The SDS-PAGEs for each resulting supernatant (having the same concentration of proteins) were performed and then immunoblot analyses thereof were carried out using anti-claudin-1, anti-occludin, and anti-ZO-1 antibodies. The results thereof are shown in FIG. 2. From the results of FIG. 2, it can be seen that the junction protein expressions in the test groups treated with the peptides of SEQ ID NOs: 1 to 3 were significantly increased, in comparison with that of the peptide non-treated group (Control group).

The invention claimed is:

1. A peptide having an activity of facilitating bindings between keratinocytes and increasing expression of junction proteins, consisting of the sequence of SEQ ID NO: 2.

2. A method for reducing skin-aging or skin-wrinkle formation, comprising applying an effective amount of a peptide consisting of the sequence of SEQ ID NO: 2 to the skin of a subject in need thereof.

3. A peptide comprising the sequence of SEQ ID NO: 1 or SEQ ID NO: 3.

4. A cosmetic composition comprising a peptide comprising the sequence of SEQ ID NO: 1 or SEQ ID NO: 3.

5. A method for reducing skin-aging or skin-wrinkle formation, comprising applying an effective amount of a peptide comprising the sequence of SEQ ID NO: 1 or SEQ ID NO: 3 to the skin of a subject in need thereof.

* * * * *

SEQUENCE LISTING

```
<160> NUMBER OF SEQ ID NOS: 4

<210> SEQ ID NO 1
<211> LENGTH: 13
<212> TYPE: PRT
<213> ORGANISM: Artificial Sequence
<220> FEATURE:
<223> OTHER INFORMATION: Synthetic peptide

<400> SEQUENCE: 1

Gly Arg Gly Asp Ser Pro Gly Arg Ala Leu Ala Arg Gly
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Synthetic peptide

<400> SEQUENCE: 2

Ala Lys Pro Thr Tyr Lys Ala Lys Pro Thr Tyr Lys Ala Lys Pro Thr
1               5                   10                  15

Tyr Lys

<210> SEQ ID NO 3
<211> LENGTH: 14
<212> TYPE: PRT
<213> ORGANISM: Artificial Sequence
<220> FEATURE:
<223> OTHER INFORMATION: Synthetic peptide

<400> SEQUENCE: 3

Ala Tyr Asp Pro Gly Tyr Lys Ala Tyr Asp Pro Gly Tyr Lys
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Gly Arg Gly Asp Ser Pro
1               5
```